United States Patent [19]

Smith

[11] Patent Number: 4,980,358

[45] Date of Patent: Dec. 25, 1990

[54] METHOD EMPLOYING GONADAL HORMONES AND DOPAMINE AGONIST INTENDED FOR COMBINED USE IN THE IMPROVEMENT OF LYMPHOCYTE FUNCTION

[75] Inventor: R. Arnold Smith, Jackson, Miss.

[73] Assignee: George D. McAdory, Jackson, Miss.

[21] Appl. No.: 494,327

[22] Filed: Mar. 16, 1990

Related U.S. Application Data

[63] Continuation-in-part of Ser. No. 177,121, Apr. 4, 1988, Pat. No. 4,929,640.

[51] Int. Cl.$^5$ .................... A01N 43/42; A01N 43/08; A61K 31/535
[52] U.S. Cl. ................................ 514/288; 514/230.2; 514/232.5; 514/234.2; 514/474; 514/254
[58] Field of Search ............ 514/474, 254, 288, 230.2, 514/232.5, 234.2

[56] References Cited

PUBLICATIONS

CA: 92(17) 140827(z).
CA: 111(5) 33245(x).

Primary Examiner—Stanley J. Friedman
Assistant Examiner—T. J. Criares
Attorney, Agent, or Firm—Epstein, Edell & Retzer

[57] ABSTRACT

A new method, useful as a pharmacologic strategy, contains a gonadal hormone in combination with a dopamine agonist such as bromocriptine, and optionally an ascorbate source. This method has a significant ability to stimulate enhanced lymphocyte function. Certain components used with the method may be combined into medicaments.

31 Claims, No Drawings

METHOD EMPLOYING GONADAL HORMONES AND DOPAMINE AGONIST INTENDED FOR COMBINED USE IN THE IMPROVEMENT OF LYMPHOCYTE FUNCTION

RELATED APPLICATIONS

The present invention is a continuation-in-part of Ser. No. 07/177,121, filed Apr. 4, 1988, now U.S. Pat. No. 4,929,640.

BACKGROUND OF THE INVENTION

Phenotypic subpopulations of lymphocytes in the peripheral blood, as defined by immunofluorescent cell sorting, are believed to reflect a useful measure of a person's immune function. For conceptual purposes the lymphocytes believed to arise from the embryonic thymus can be divided into a regulatory group and an effector group. The regulatory group is typified by the OKT-3, OKT-11, OKT-4 and OKT-8 monoclonal antibodies to human leucocytes. These monoclonal antibodies are currently marketed through the Colter Company. A clinically significant problem without ready solution is represented by a tendency of these phenotypes to fall below normal limits in several types of disease including autoimmune illness and neoplasia. The present invention, suspected to act through the hypophysis (pituitary gland) by the stimulation of somatotropin, has been found to significantly increase the OKT phenotypes designated above and, in the course of this enhancing effect, to successfully relieve or improve many autoimmune illnesses.

The life cycle decline of somatotropin may be a fundamental cause of many medical ailments as is suggested by the wide range of somatic complaints which respond to the method of treatment of the instant invention. Included in these somatic complaints are connective tissue inflammations such as arthritis, tendonitis, bursitis, and myositis; migraine headaches, tension headaches or sinus headaches; inflammatory conditions involving adenomatous viscera, including breast, lung, urinary bladder, liver and bowel; and psychological depression typically accompanying many of these conditions.

DESCRIPTION OF THE INVENTION

The present invention relates to medicament formulations and their use to stimulate regulatory lymphocyte populations, the medicaments containing: (1) a gonadal hormone, (2) a dopamine agonist and, optionally, (3) an ascorbate salt such as sodium ascorbate (Vitamin C).

Suitable gonadal hormones for administration in accordance with the compositions and methods of the instant invention include progestins, andogens and estrogens or combinations thereof. Estrogenic hormones are the preferred gonadal hormones for use in the compositions and methods of treatment in the instant invention, preferably; equine conjugated estrogen, estrone, piperazine estrone sulfate and the like. Preferred andogen hormones include testosterone, methyl testosterone and the like. Preferred progestin hormones include medroxyprogesterone acetate, natural progesterone and the like. It is believed that all synthetic or natural gonadal hormones, namely, the synthetic or natural estrogen, andogen and progestin hormones, are instrumental in therapeutically adequate amounts in initiating and/or focusing an attack of natural killer lymphocyte immunity effectors in accordance with the method of the present invention. Gonadal hormones are administered in accordance with the methods of the present invention conjointly or sequentially with the dopamine agonist and, optionally the ascorbate, in therapeutically effective amounts ranging from 0.1 to 800 milligrams on a daily basis. Such therapeutically effective amounts vary for each type of gonadal hormone and the following amounts represent preferred therapeutic amounts for the preferred gonadal hormones.

| GONADAL HORMONE | MILLIGRAMS |
| --- | --- |
| Equine conjugated estrogen | 0.1 to 6.0 mg |
| Medroxyprogesterone acetate | 1.0 to 60 mg |
| Piperazine estrone sulfate (Estropipate) | 0.1 to 5 mg |
| Natural progesterone | 5.0 to 800 mg |
| Methyltestosterone | 1.0 to 20 mg |
| Estrone | 1.0 to 10 mg |

Suitable dopamine agonists for use in the instant invention are dopaminergic ergot alkaloids such as bromocriptine, lergotrile or pergolide or pharmaceutically acceptable salts thereof or combinations thereof. The preferred dopamine agonist for use in the present invention is bromocriptine or pharmaceutically acceptable salts thereof such as bromocriptine mesylate.

The dopamine agonists are administered to humans in the above active compounds, preferably bromocriptine, in amounts sufficient to stimulate regulatory lymphocyte populations, namely, amounts ranging from approximately 0.4 to 10.0 milligrams daily, preferably from 0.6 to 5.0 milligrams daily.

The ascorbate source when administered in combination with the formulation of the present invention is typically administered in the form of ascorbic acid, sodium ascorbate, or other equivalent salt forms in somatotropin producing amounts typically ranging from 0.25 grams to 20 grams on a daily basis. It has been determined that the ratio of weight of ascorbate to bromocriptine during administration of 400:1 or greater is preferred.

A preferred composition of the present invention additionally includes 0.1 to 0.3 mg of thyroxin or equivalent, physiologic mixtures of thyroxine and liothyronine are often employed to further improve both regulatory and effector lymphocyte function.

The pharmaceutical compositions of the present invention may be coadministered in a single blended formulation or the individual components may be sequentially administered. The drugs of the instant invention are preferably orally administered, in the form of troches, tablets, capsules and the like, however, other modes of administration are considered to be within the scope of the present invention.

The medicament combination of the present invention produces a delayed desired clinical effect with the onset of benefit usually occurring not sooner than ten days, and at times as long as two months before energy improves in the patient and the first signs of symptomatic improvement occur. After two months the beneficial effects of treatment are usually well established. The clinical pattern suggests a rate limited induction process, with a threshold of subjective response being reached after a variable delay.

Somatotropin is a polypeptide hormone currently available for pharmacological use only at great cost and is made either from human pituitary gland fractionation or through recombinant cell culture technology. Exogenous somatotropin is digested in the stomach and does not cross mucosal surfaces well, thus requiring inconvenient intramuscular or intravenous injection. Thus exogenous replacement is both expensive and, like insulin, clinically demanding in its delivery. The composition of the present invention, by stimulating endogenous production, is a much more satisfactory method for treatment of somatotropin deficiency.

The gonadal hormone-dopamine agonist combination may be used alone or in combination with pharmacological doses of vitamin C, as an initial induction of regulatory function. After one month of initial induction, further additions can be usefully added. To understand this sequencing one must consider the basic lymphocyte subsets in the regulatory group of OKT reactive surface antibodies mentioned above. Two regulatory lymphocyte subsets that are often depressed in autoimmune disease are the OKT-11 and OKT-8 phenotypes. The suppressor T (thymus gland) lymphocyte (OKT-8) population suppresses effector attack on auto-antigens, thus protecting the individual's own vital tissues. Healthful levels of somatotropin secretion depend on tonic stimulation of cells in the adenohypophysis by dopamine of central nervous system origin, and the thymus in turn produces hormones depending on tonic stimulation by somatotropin. Suppressor T-lymphocytes are held in tonic adequacy in turn by thymic hormone secretion. The well documented life cycle decline in thymic hormone is predominately peripheral to the level of action of this invention, but is a component of the deficiency sequence restored or rejuvenated by the present invention. It is believed that the trophic effect of the steroidal hormone, DHEA, induced by the secretagogue ascorbate, and the trophic and regulation effects of the gonadal hormone group (estrogen, androgen, and progestin described above) do perform an essential and often complementary supporting role to the thymic epithelial cell population, thereof augmenting the release of differentiating hormones focused toward the thymic derived lymphocyte population. The novel method of the present invention acts early and later in this physiologic sequence at the level of dopaminergic input to the hypophysis and at the thymus.

Without the suppressor cell component of regulatory function at adequate levels, auto-immune illness often develops. Attempts at stimulating the effector (i.e., natural killer) component of the lymphocyte population (Leu 11 or Leu 7) without adequate regulatory function usually result in increased attacks on auto-antigens with flare-ups of autoimmune related illnesses and an increase in malaise. The helper inducer population OKT-4 acts as a spotter mechanism to focus immune effectors on the enemy antigen, and the immune system is unable to achieve specificity with helper inducer T-cell inadequacy. On the other hand, once the helper inducer lymphocyte population (OKT-4) and suppressor cytotoxic T-lymphocyte suppressor/cytotoxic lymphocyte subsets are restored in accordance with the present invention, then one can begin effective stimulation of the effector lymphocyte subsets with confidence that the patient's condition will not be significantly worsened but that invaders, such as viral illnesses or neoplasia, will be more effectively opposed. The effector group of lymphocytes is typified by the Leu 11 phenotypic marker (Becton Dickinson) and is believed to be significantly under leutinizing hormone control. The unique compositions of the present invention result in the restoration of regulatory functions that allow high doses of gonadal hormones to be used with greatly reduced auto-immune side effects.

Pharmacological studies employing (1) clinical response and (2) objective assessment by immunofluorescent lymphocyte phenotyping have proven unequivocally that the composition of the present invention is efficacious and that the effects obtained seem significantly better than clinical benefits obtained by many other types of medications that attempt to attack disease processes more peripherally in their pathophysiologic mechanism of causation. Complete blood count ("CBC") determinations can be used to monitor the percentage of lymphocytes in peripheral blood, or to calculate the absolute lymphocyte count (percent lymphocytes$\times 0.1 \times$white blood count). This conventional test has little, if any, value in monitoring efficacy of the composition of the present invention, and the importance of immunofluorescent phenotyping for objective assessment must again be stressed.

The quantities of gonadal hormone and bromocriptine or other equivalent dopamine agonist described herein have been well documented as safe and acceptable for long term use when used independently of one another. Use of a combination in the quantities and ratio employed in the present invention has not been described in the prior art. While the combination of a gonadal hormone, a dopamine agonist and, optionally ascorbate (e.g. estrogen, bromocriptine and sodium ascorbate) seems to be quintessential to the effects described herein, the addition of dl-alpha-tocopherol (vitamin E) in the quantity of 400 international units, three times daily, appears to provide a moderate improvement in the patient's response rate. For patients with severe allergies, riboflavin (vitamin B2), 100 milligrams once or twice daily, was also employed.

The following examples set out details of preferred composition formulas suitable for use in the present invention, it being understood that further preparations suitable for the present invention may also be employed.

EXAMPLE 1

Tablets according to the formula: sodium ascorbate, 500 mg; bromocriptine, 0.21 mg; dl-alphatocopherol, 100 international units; equine conjugated estrogen, 0.21 mg.

EXAMPLE 2

Tablets according to the formula: sodium ascorbate, 500 mg; bromocriptine, 0.1 mg; dl-alpha-tocopherol, 50 international units; equine conjugated estrogen, 0.21 mg.

EXAMPLE 3

Tablets according to the formula sodium ascorbate, 1 gm; bromocriptine, 0.1 mg; dl-alpha-tocopherol, 60 international units; equine conjugated estrogen, 0.21 mg.

EXAMPLE 4

Tablets according to the formula: bromocriptine, 0.1 mg;; equine conjugated estrogen, 0.21 mg.

The above examples are typical of compositions employed during the induction phase, and starting dose would typically be one tablet, twice daily, increasing up to as many as twenty-four tablets daily in three to four divided doses. The examples which follow are compositions employed once the rate-limited induction of regulatory function in the somatotropin dependent lymphocyte phenotypes has been established.

EXAMPLE 5

Examples 1, 2 and 3 above with the addition of medroxyprogesterone acetate 1.0 mg.

EXAMPLE 6

Sodium ascorbate, 500 mg; bromocriptine, 0.21 mg; dl-alpha-tocopherol, 100 international units; medroxyprogesterone acetate, 1.0 g.

EXAMPLE 7

Sodium ascorbate, 500 mg; bromocriptine, 0.21 mg; dl-alpha-tocopherol, 100 international units; equine conjugated estrogen, 0.11 mg; norethindrone acetate ( a progestin) 0.5 mg.

EXAMPLE 8

Sodium ascorbate, 500 mg; bromocriptine, 0.21 mg; dl-alpha-tocopherol, 100 international units; megestrol acetate, 14 mg; germanium sesquioxide, 25 mg.

EXAMPLE 9

A preferred troche for use in the method of the instant invention for treatment of autoimmune disease is as follows:
1. germanium sesquioxide, 50 mg
2. coenzyme Q-10, 50 mg
3. bromocriptine, 2.5 mg
4. equine conugated estrogen, 2.5 mg
5. natural progesterone, 50 mg
6 methyl testosterone, 5 mg
7. selenium, 100 micro grams
8. vitamin B-12, 100 micro grams
9. levothyroxine sodium, 0.2 mg
10. liothyronine, 50 micro grams Patients are given 500 mg. of an ascorbate separately either as sodium ascorbate or as buffered vitamin C powder (a commercial mixture which when mixed with an aqueous solution produces calcium, magnesium, and potassium ascorbates). Vitamin E is also prescribed separately as three, 400 IU capsules per day in divided doses.

EXAMPLE 10

The formulation of Example 9 modified for intensive effector cytotoxic cell stimulation replacing ingredients 4, 5 and 6 with medroxyprogesterone acetate, 30 mg. and coadminstering suitable dosages of sodium ascorbate or buffered vitamin C powder, and the vitamin E as in Example 8. Optionally, a suppressor T-cell blocker such as cimetidine may be coadminstered for a cancer patient's cytotoxic T-cell stimulation.

Although the above examples employ the dopaminergic ergot alkaloid known as bromocriptine (i.e., 2-bromo-alphaergocryptine), sold commercially as Paradel, it is believed that other dopamine agonists, having the capacity to stimulate regulatory lymphocyte populations, are appropriate substitutes; lergotrile and pergolide, are examples of such dopamine agonists.

The present invention produces numerous advantageous results. For example, it provides a clinically reliable method for stimulating growth hormone production in the intact hypophysis. The pharmaceutical composition is also useful in stimulating regulatory lymphocyte subsets likely dependent on somatotropin stimulation of the thymus gland.

In addition, the composition produces improvement of both regulatory and effector lymphocyte function. Germanium sesquioxide, a potent stimulant of Leu 11 lymphocytes, and Coenzyme Q-10, a general immune stimulant, are both substances which facilitate electron transport in mitochondrial enzyme systems, and both facilitate the immune enhancement derived from this basic method described above. Similarly Vitamin E (dl alpha tocopheral acetate) is used for its well documented helper T-cell stimulatory effect. In other words, the dopaminergic agonist when combined with the administration of gonadal hormones and optionally, an ascorbate source, can, by virtue of the enhancement of regulatory function, produce a more focused attack of natural killer lymphocyte immunity effectors against invaders disruptive to the internal homeostasis and this basic combination does not exclude the use of or the benefit from further immune stimulants described immediately above which serve as secondary adjuvants.

The compositions of the present invention are also believed to be effective to: relieve or improve inflammatory mesenchymal disorders such as arthritis, tendonitis, bursitis, and myositis; relieve auto-immune mediated inflammatory glandular disorders such as pancreatitis, interstitial cystitis, ulcerative colitis, chronic immune hepatitis and immune pneumonitis; relieve or improve auto-immune epidermal disorders such as alopecia areata or scleroderma; enhance general immune resistance to chronic viral infections such as those mediated by the herpes viridae group (Type 1 Herpes, Type 2 Herpes, Epstein-Barr Viruses, cytomegalo-virus); improve the results of progestin or androgen mediated enhancement of natural killer T-cell function by first improving the regulatory function typified by the OKT-4 group of helper-induced lymphocytes which focuses effector activity correctly against desired targets and by stimulating suppressor/cytotoxic OKT-8 T-lymphocyte population which prevents misdirected attacks of effector cells o autoantigens resulting in autoimmunity; prevent recurrent migraine headaches; relieve or improve sexual behavior problems relating to sexual disfunction such as impotency in males and frigidity in females; relieve or improve excessive breast tenderness, engorgement or glandular stimulation as a side effect from estrogen replacement therapy thereby permitting higher dosages of estrogen to be utilized during estrogen replacement therapy; and improve the loss of physical strength, loss of energy, and psychological depression which accompany disturbances of somatotropin secretion.

Treatment by the novel pharmaceutical composition of the present invention, by enhancing suppressor T-cell function, decreases the sensitivity of auto-antigens to allergic attacks instituted by various environmental allergens. For this reason the present invention is useful in treating patients suffering from severe allergic disease. Moreover, many hypochondriacs prove to have organic disease, as documented by quantifiable regulatory subset determinations below the normal range. These patients, too, will often improve when treated in accordance with the present invention.

The composition of the present invention also appears to stimulate growth of preadolescent youth.

Because of the relationship of dopaminergic exhaustion to prominent types of drug addiction (cocaine, heroine, crack), and because the composition of the present invention supports restoration of an extremely important part of dopaminergic function (i.e., growth hormone secretion), the composition appears to serve a useful role in the treatment of some common forms of drug abuse. Moreover, a principle intuitive incentive to cigarette and other tobacco addiction is the pharmacological benefit obtained by somatotropin secretagogue equivalency in tobacco. The principle problem with tobacco smoke is that it contains a plethora of highly reactive pyrochemical species that denature normal physiologic molecules, such as those of mesenchymal support, causing aging and, in chromosomes, greatly increasing gene mutation rate. A person who is a long term cigarette user faces the choice of either continuing this dangerous habit or of terminating smoking. Smoking termination, by allowing a drop in somatotropin-induced regulatory lymphocyte function, may actually encourage certain latent cancers in various stages of initiation or promotion to grow uncontrollably. Somatotropin loss also causes physiological depression, irritability, increased body fat with weight gain, and a loss in muscle mass with decrease in strength and energy. The pharmaceutical composition of the present invention, by substantially replacing the active principle of tobacco smoke in a vastly more healthful manner, may contribute greatly to efforts to prevent or decrease tobacco use. The antioxidant properties of ascorbate stand in marked contrast to the pro-oxidant properties of pyrochemicals like those in tobacco smoke.

The compositions of the present invention are also useful for their somatotropin secretagogue effects for use in weight loss programs for overweight humans as the effects of these compositions counteract somatotropin loss effects as discussed above including depression; irritability and increased body fat with weight gain. It has also been determined that a dopamine agonist, preferably bromocriptine, and an ascorbate source in the amounts previously discussed in the absence of a gonadal hormone is useful weight loss programs, in both promoting fat loss and in controlling undesirable side effects such as depression and irritability. There is a specific somatotype often seen in prostate cancer patients, melanoma patients, and in many breast cancer patients of increased truncel distributions of fat. Often the belly seem protuberant or "bloated". This may be described as the "Santa Claus physique" or less exaggerated varients. This invention by its somatotropin stimulation property may cause resorption of this fat, a replacement of fat with muscle, and return of a more youthful physique. Body weight can be conceptualized to exist in different compartments; this invention reduces the fatty compartment and augments the muscle compartment.

Even though local recurrence of radically resected cancer of breast or rectum is an initial manifestation of failure that may be a fatal development, and even though regional radiotherapy often decreases the frequency of regional relapse, the long-term survival of adjuvantly irradiated patients with these conditions is not significantly improved in most studies. The major mechanism of this failure to improve survival rate is the decimation of committed lymphocytes in the irradiated volume and the defective immunity consequent to radiotherapy. Immune depression after radiotherapy is documented in the literature. By stimulating enhanced lymphocyte function, the composition of the present invention has a potential role in reconstituting immunity in these patients and in other post-radiotherapy immunologically depressed subjects.

It is also believed that the composition of the present invention tends to retard the destructive components of the aging process to a significant degree. The antioxidant properties of ascorbate, in and of itself, may be useful to some extent in enhancing a sense of well-being; however, when combined with bromocriptine or equivalent dopamine agonist and a gonadal hormone, the immune stimulatory effect of somatotropin production and the thymic epithelial competency induced by this method produces a far more effective clinical treatment. This material can, therefore, justify general use for those individuals who wish to retard the aging process and who find relief of disease objectively and subjectively manifest during the first two months of a therapeutic trial.

Having described preferred embodiments of a new method and associated medicaments intended for combined use in the improvement of lymphocyte function under this method, it is believed that other modifications, variations and changes will be suggested to those skilled in the art in view of the teachings set forth herein. It is therefore to be understood that all such variations, modifications and changes are believed to fall within the scope cf the present invention as described by the appended claims.

What is claimed is:

1. A pharmaceutical composition useful in enhancing stimulated lymphocyte function comprising a dopamine agonist selected from the group consisting of bromoncriptine, lergotrile and pergolide or pharmaceutically acceptable salts thereof and a gonadal hormone selected from the group consisting of progestinic, androgenic or estrogenic hormones, in therapeutically effective amounts.

2. The composition according to claim 1 wherein the dopamine agonist is bromocriptine or a pharmaceutically acceptable salt thereof.

3. The composition according to claim 1 wherein the gonadal hormone is an estrogenic hormone.

4. The composition according to claim 3 wherein the estrogen hormone is selected from the group consisting of equine conjugated estrogenic, estrone or piperazine estrone sulfate.

5. The composition according to claim 1 wherein the gonadal hormone is an andogenic hormone.

6. The composition according to claim 1 wherein the gonadal hormone is a progestinic hormone 7. The composition according to claim 6 wherein the progestinic hormone is medroxyprogesterone acetate.

8. The composition according to claim 6 wherein the progestinic hormone is natural progesterone.

9. The composition according to claim 1 comprising 0.1 to 300 milligrams of the gonadal hormone.

10. The composition according to claim 1 comprising 0.4 to 10 milligrams of the dopamine agonist.

11. The composition according to claim 1 additionally comprising an ascorbate salt.

12. The composition according to claim 11 wherein the ascorbate salt is sodium ascorbate.

13. The composition according to claim 11 comprising 0.25 to 20 grams of the ascorbate salt.

14. A method for stimulating enhanced lymphocyte function in human beings requiring such treatment comprising administering to said human being a dopamine agonist compound selected from the group consisting of bromocriptine, lergotrile and pergolide or pharmaceutically acceptable salts thereof and a gonadal hormone selected from the group consisting of progestinic, androgenic or estrogenic hormone in amounts sufficient to stimulate regulatory lymphocyte populations 15. The method as defined in claim 14 wherein the dopamine agonist is administered in an amount ranging from about 0.6 to 5.0 milligrams.

16. The method as defined in claim 14 wherein the dopamine agonist is bromocriptine.

17. The method of claim 14 wherein the stimulated enhanced lymphocyte function is used in the treatment of humans suffering from inflammatory mesenchymal disorders.

18. The method of claim 14 wherein the stimulated enhanced lymphocyte function is used in the treatment of humans suffering from auto-immune media&ed inflammatory glandular disorders.

19. The method of claim 14 wherein the stimulated enhanced lymphocyte function is used in the treatment of humans suffering from auto-immune epidermal disorders.

20. The method of claim 14 wherein the stimulated enhanced lymphocyte function is used in the treatment of humans suffering from decreased immune resistance to chronic viral infections.

21. The method of claim 14 wherein the stimulated enhanced lymphocyte function is used in the treatment of humans suffering from recurrent migraine headaches.

22. The method of claim 14 wherein the stimulated enhanced lymphocyte function is used in the treatment of humans suffering from loss of physical strength, loss of energy and psychological depression associated with disturbances of somatotropin secretion 23. The method of claim 14 wherein the stimulated enhanced lymphocyte function is used in the treatment of humans suffering from severe allergies.

24. The method of claim 14 wherein the stimulated enhanced lymphocyte function is used in the treatment of humans suffering from drug abuse.

25. The method as defined in claim 14 additionally comprising administration of at least one compound from the group consisting of an ascorbate salt, thyroxin, riboflavin dl-alpha tocopherol, germanium sesquioxide, and by coenzyme Q-10.

26. The method of claim 14 wherein the stimulated enhanced lymphocyte function is used in a weight loss and or weight redistribution treatment for overweight human beings.

27. A method for stimulating enhanced lymphocyte function and somatotropin secretagogue effects in overweight human beings on a weight loss program comprising coadministering to said overweight human beings a dopamine agonist selected from the group consisting of bromocriptine, lergotrile and pergolide or pharmaceutically acceptable salts thereof, and an ascorbate source in an amount sufficient to stimulate regulatory lymphocyte populations to enhance somatotropin production.

28. The composition according to claim 1 additionally comprising thyroxin.

29. The composition according to claim 28 additionally comprising 0.1 to 0.3 mg of thyroxin.

30. The method of claim 14 wherein the stimulated enhanced lymphocyte function is used in the treatment of humans suffering from impotency or frigidity.

31. The method of claim 14 wherein the stimulated enhanced lymphocyte function is used in the treatment of humans suffering from excessive breast &tenderness, engorgement or glandular stimulation as a side effect from estrogen replacement therapy.

* * * * *